United States Patent
Nishio

(10) Patent No.: US 11,241,251 B2
(45) Date of Patent: Feb. 8, 2022

(54) MEDICAL DEVICE

(71) Applicant: TERUMO KABUSHIKI KAISHA, Tokyo (JP)

(72) Inventor: Kousuke Nishio, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 176 days.

(21) Appl. No.: 16/351,673

(22) Filed: Mar. 13, 2019

(65) Prior Publication Data
US 2019/0209205 A1    Jul. 11, 2019

Related U.S. Application Data

(63) Continuation of application No. PCT/JP2017/032329, filed on Sep. 7, 2017.

(30) Foreign Application Priority Data

Sep. 16, 2016  (JP) .............................. JP2016-182403

(51) Int. Cl.
*A61B 17/3207* (2006.01)
*A61B 17/00* (2006.01)
*A61B 17/32* (2006.01)

(52) U.S. Cl.
CPC .............. *A61B 17/320758* (2013.01); *A61B 2017/00309* (2013.01); *A61B 2017/00318* (2013.01);
(Continued)

(58) Field of Classification Search
CPC .. A61B 17/320758; A61B 2017/00309; A61B 2017/320766; A61B 2017/00318;
(Continued)

(56) References Cited

U.S. PATENT DOCUMENTS

| 6,565,588 | B1 | 5/2003 | Clement et al. |
| 6,579,298 | B1 * | 6/2003 | Bruneau ........ A61B 17/320758 |
| | | | 606/159 |

(Continued)

FOREIGN PATENT DOCUMENTS

| CN | 101522115 A | 9/2009 |
| CN | 101711131 A | 5/2010 |

(Continued)

OTHER PUBLICATIONS

International Search Report (PCT/ISA/210) dated Dec. 5, 2017, by the Japanese Patent Office as the International Searching Authority for International Application No. PCT/JP2017/032329.

(Continued)

*Primary Examiner* — Richard G Louis
(74) *Attorney, Agent, or Firm* — Buchanan Ingersoll & Rooney PC

(57) ABSTRACT

A medical device is disclosed for cutting an object in a body lumen, including: a rotation structure which includes a cutting portion; a first shaft which is connected to a center shaft of the rotation structure and drives the rotation of the rotation structure; and a second shaft which is formed in a tubular shape surrounding the first shaft, wherein the second shaft is bendable at two positions including a first curved portion and a second curved portion located more distal than the first curved portion, and the second shaft is rotatable in a state in which a proximal side of the first curved portion and a distal side of the second curved portion of the second shaft are kept substantially parallel to each other.

21 Claims, 7 Drawing Sheets

(52) U.S. Cl.
CPC ............. *A61B 2017/320004* (2013.01); *A61B 2017/320052* (2013.01); *A61B 2017/320733* (2013.01); *A61B 2017/320766* (2013.01)

(58) Field of Classification Search
CPC ....... A61B 2017/320052; A61B 2017/320733; A61B 2017/320004
See application file for complete search history.

(56) References Cited

U.S. PATENT DOCUMENTS

| | | | |
|---|---|---|---|
| 2002/0077642 A1* | 6/2002 | Patel ............. | A61B 17/320758 606/167 |
| 2008/0097499 A1 | 4/2008 | Nash et al. | |
| 2008/0306498 A1 | 12/2008 | Thatcher et al. | |
| 2009/0018565 A1* | 1/2009 | To .................. | A61B 17/320758 606/159 |
| 2012/0109171 A1 | 5/2012 | Zeroni et al. | |
| 2013/0060270 A1 | 3/2013 | Teeslink et al. | |
| 2015/0141816 A1* | 5/2015 | Gupta ............. | A61B 17/32002 600/427 |
| 2016/0213397 A1 | 7/2016 | Shturman | |

FOREIGN PATENT DOCUMENTS

| | | |
|---|---|---|
| CN | 102905634 A | 1/2013 |
| CN | 103200886 A | 7/2013 |
| JP | 2011500151 A | 1/2011 |
| JP | 2014501552 A | 1/2014 |
| WO | 2008/042987 A2 | 4/2008 |
| WO | 2016007652 A1 | 1/2016 |

OTHER PUBLICATIONS

Written Opinion (PCT/ISA/237) dated Dec. 5, 2017, by the Japanese Patent Office as the International Searching Authority for International Application No. PCT/JP2017/032329.

Office Action (The First Office Action) dated Feb. 3, 2021, by the National Intellectual Property Administration in corresponding Chinese Patent Application No. 201780057050.5 and an English Translation of the Office Action. (12 pages).

Office Action (The Second Office Action) dated Sep. 23, 2021, by the State Intellectual Property Office of People's Republic of China in corresponding Chinese Patent Application No. 201780057050.5 and an English Translation of the Office Action. (15 pages).

* cited by examiner

MEDICAL DEVICE

CROSS-REFERENCES TO RELATED APPLICATIONS

This application is a continuation of International Application No. PCT/JP2017/032329 filed on Sep. 7, 2017, which claims priority to Japanese Application No. 2016-182403 filed on Sep. 16, 2016, the entire content of both of which is incorporated herein by reference.

TECHNICAL FIELD

The present disclosure generally relates to a medical device.

BACKGROUND DISCUSSION

Atherectomy is an important treatment for improving arterial patency after treatment. As the atherectomy, a method of cutting and removing a stenotic object by bringing a rotation body into contact with the stenotic body is mainly adopted nowadays (for example, see U.S. Pat. No. 6,565,588).

However, since there is a possibility that a portion of the cutting device having a cutting function reaches a deep portion of the blood vessel when the force of the rotation body is applied to the stenotic object, there is a concern that the blood vessel may be punctured.

In order to solve the above-described problems, an atherectomy device capable of bending a distal portion and cutting a stenotic object after defining the directionality are known. However, since a direction defined when advancing a catheter can be easily shifted (or changed), a torque applied may not be effectively used when a user tries to define the direction by twisting the catheter by a hand.

SUMMARY

A medical device is disclosed capable of defining a directionality and cutting a stenotic object while securing a sufficient torque effect.

An embodiment of the present disclosure is directed to a medical device for cutting an object in a body lumen, including: a rotation structure which includes a cutting portion; a first shaft which is connected to a center shaft of the rotation structure and configured to drive the rotation of the rotation structure; and a second shaft which is formed in a tubular shape surrounding the first shaft, wherein the second shaft is bendable at two positions including a first curved portion and a second curved portion located more distal than the first curved portion, and the second shaft is configured to be rotatable in a state in which a proximal side of the first curved portion and a distal side of the second curved portion of the second shaft are kept substantially parallel to each other.

According to an embodiment of the present disclosure, a rotation locus of the second shaft is preferably located outside a rotation locus of the first shaft.

According to an embodiment of the present disclosure, in a state in which the second shaft is bent, a side of the second shaft more proximal than the first curved portion is preferably pressed against an inner wall of a body lumen and the rotation structure is preferably located opposite to the first curved portion in the body lumen.

According to an embodiment of the present disclosure, the rotation of the first shaft and the second shaft is preferably driven by a drive device.

According to an embodiment of the present disclosure, the second shaft preferably rotates at a speed lower than that of the first shaft.

According to an embodiment of the present disclosure, the rotation speed of the first shaft is preferably 10,000 rpm (revolutions per minute) to 120,000 rpm and the rotation speed of the second shaft is preferably 5 rpm to 10,000 rpm.

The medical device according to an embodiment of the present disclosure preferably further includes a bearing which is disposed between the rotation structure and the second shaft and the second shaft is preferably bent by a force transmitted from the rotation structure through the bearing when the first shaft is pulled.

According to an embodiment of the present disclosure, the bearing is preferred not to be rotationally symmetric with respect to a rotation axis of the rotation structure and the second shaft is preferably bent when the rotation structure comes into contact with only a circumferential direction part of the bearing.

According to an embodiment of the present disclosure, a rotation axis of the second shaft is preferably different from a rotation axis of the first shaft.

According to an embodiment of the present disclosure, the rotation locus of the second shaft is preferably larger than the rotation locus of the first shaft.

According to an embodiment of the present disclosure, the second shaft preferably has a slit, which makes the second shaft bendable.

According to an embodiment of the present disclosure, the second shaft preferably has a bending tendency, which makes the second shaft bendable.

The medical device according to an embodiment of the present disclosure preferably further includes an outer sheath, which has a tubular shape surrounding the second shaft.

According to an embodiment of the present disclosure, the second shaft is preferably rotatable in a direction opposite to the rotation direction of the first shaft.

According to an embodiment of the present disclosure, the outer surface of the second shaft is preferably a non-cutting portion.

According to the medical device of the present disclosure, it is possible to define a directionality and to cut a stenotic object while securing a sufficient torque effect.

In accordance with an aspect, a medical device for cutting an object in a body lumen, the medical device comprising: a rotation structure having a cutting portion; a first shaft configured to be connected to a center shaft of the rotation structure and configured to drive a rotation of the rotation structure; a second shaft having a tubular shape, the second shaft configured to surround the first shaft, the second shaft configured to be bendable at two positions including a first curved portion and a second curved portion, the second curved portion being located distally of the first curved portion; and wherein the second shaft is configured to be rotatable in a state in which a proximal side of the first curved portion and a distal side of the second curved portion of the second shaft are kept substantially parallel to each other.

In accordance with another aspect, a medical device for cutting an object in a body lumen, the medical device comprising: a rotation structure having a cutting portion; a first shaft configured to be connected to a center shaft of the rotation structure and configured to drive a rotation of the rotation structure; a second shaft having a tubular shape, the second shaft configured to surround the first shaft and configured to be bendable at two positions including a first curved portion and a second curved portion, the second curved portion being located distally of the first curved portion; and a bearing which is disposed between the rotation structure and the second shaft, and wherein the second shaft is bent by a force transmitted from the rotation structure through the bearing when the first shaft is pulled.

In accordance with a further aspect, a method for cutting substances inside a body lumen using a medical device including a rotation structure having a cutting portion, a first shaft configured to be connected to a center shaft of the rotation structure and configured to drive a rotation of the rotation structure, and a second shaft having a tubular shape, the second shaft configured to surround the first shaft, the second shaft configured to be bendable at two positions including a first curved portion and a second curved portion, the second curved portion being located distally of the first curved portion, the method comprising: inserting the medical device into the body lumen; rotating the second shaft in a state in which a proximal side of the first curved portion and a distal side of the second curved portion of the second shaft are kept substantially parallel to each other; and cutting the substances inside the body lumen.

DESCRIPTION OF EMBODIMENTS

Figure 1:
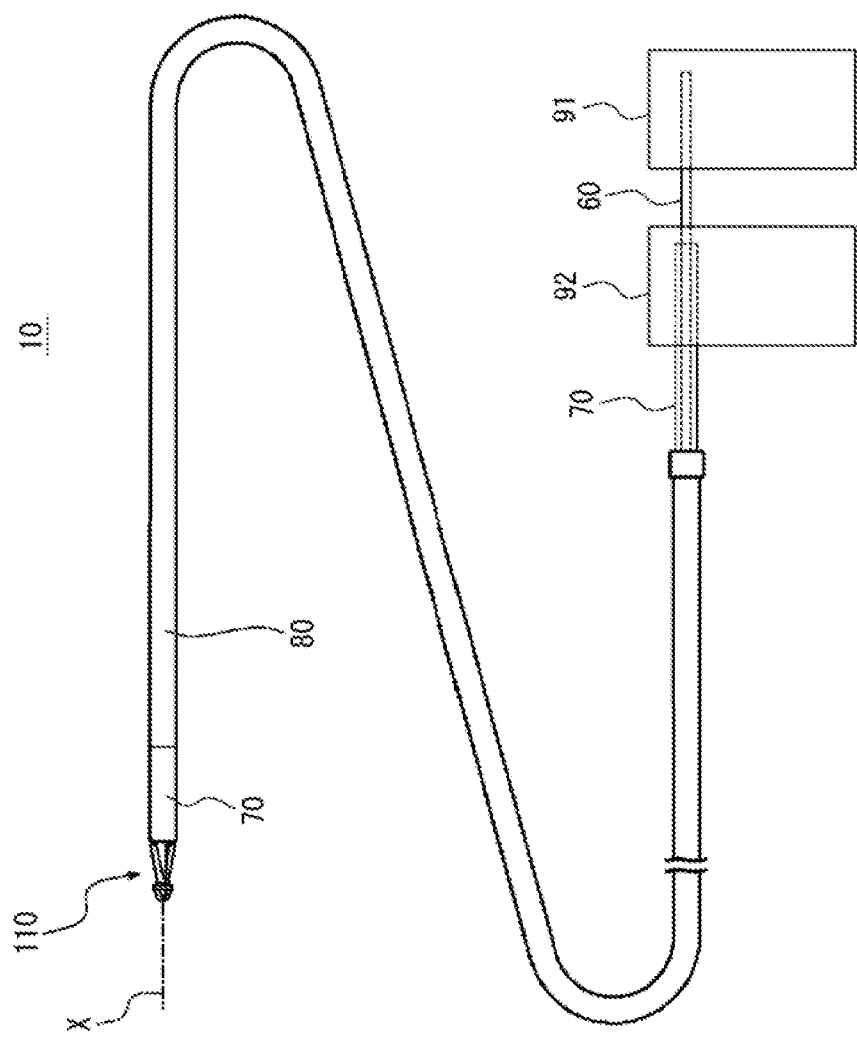
FIG. 1 is a diagram illustrating a medical device according to an embodiment of the present disclosure.

Hereinafter, an embodiment of the present disclosure will be described with reference to the drawings. Dimension ratios in the drawings may be exaggerated and may differ from actual ratios for convenience of description. Further, in each drawing, common members are denoted by the same reference numerals. Further, in this specification, the side to be inserted into the blood vessel of the medical device will be referred to as the "distal side" and the side to be operated will be referred to as the "proximal side".

Figure 2:
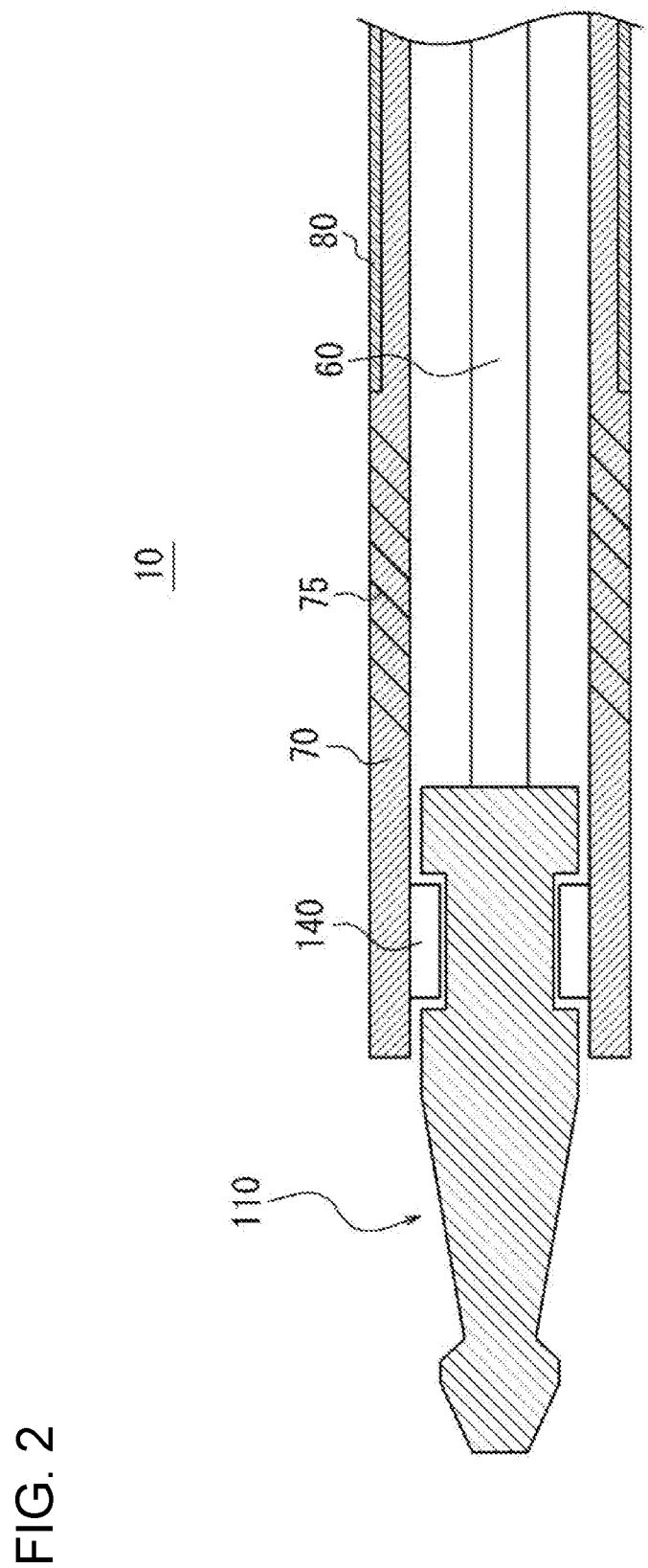
FIG. 2 is an enlarged cross-sectional view of a distal side of the medical device illustrated in FIG. 1.

First, a configuration of a medical device according to an embodiment of the present disclosure will be described with reference to FIGS. 1 and 2. FIG. 1 is a diagram illustrating a medical device 10 according to an embodiment of the present disclosure. FIG. 2 is an enlarged cross-sectional view of the distal side of the medical device 10 illustrated in FIG. 1.

In accordance with an exemplary embodiment, the medical device 10 is used in a treatment of cutting an object inside a body lumen, for example, a treatment of cutting a stenotic object caused by plaque and thrombus inside a blood vessel. Next, a case of cutting a stenotic object inside a blood vessel will be described as a detailed example.

In accordance with an exemplary embodiment, the medical device 10 can include, as illustrated in FIG. 1, a rotation structure 110 which is rotatable along a rotation axis X and is able to cut a stenotic object, a first shaft 60 which drives the rotation of the rotation structure 110, a second shaft 70 which has a tubular shape and surrounds the first shaft 60, an outer sheath 80 which surrounds the second shaft 70 and has a tubular shape, a first drive device 91 which operates the first shaft 60, and a second drive device 92 which operates the second shaft 70.

As illustrated in FIG. 2, since the first shaft 60 is connected to the center shaft of the rotation structure 110, the rotation structure 110 rotates by the driving of the first shaft 60 when the first shaft 60 rotates. The rotation of the first shaft 60 is controlled by the first drive device 91 illustrated in FIG. 1. Hereinafter, the rotation of the first shaft 60 and the rotation of the rotation structure 110 will be referred to as "spin". Further, the rotation of the second shaft 70 is controlled by the second drive device 92 illustrated in FIG. 1 independently from the first shaft 60. Hereinafter, the rotation of the second shaft 70 will be referred to as "revolution". The second shaft 70 has a slit 75, which defines a bending direction when the second shaft 70 is bent. As illustrated in FIG. 2, a bearing 140 is provided between the rotation structure 110 and the second shaft 70. Since the bearing 140 is provided, the rotation structure 110 is rather smoothly rotatable with respect to the second shaft 70.

A detailed structure of the rotation structure 110 will be described later.

The first shaft 60 is formed in a tubular shape. The distal side of the first shaft 60 is fixed to the rotation structure 110 and the proximal side of the first shaft 60 is connected to the first drive device 91 as illustrated in FIG. 1.

The first drive shaft 60 is flexible and has a characteristic in which a rotational force exerted at the proximal side is transmitted to the distal side. The first drive shaft 60 has, for example, a configuration in which a reinforcement member such as a wire formed of polyolefin such as polyethylene and polypropylene, polyamide, polyester such as polyethylene terephthalate, fluorine-based polymer such as ETFE, polyetheretherketone (PEEK), polyimide, or a combination of polyolefin, polyester, fluorine-based polymer, polyetheretherketone (PEEK), and/or polyimide is buried in a multi-layer coiled tubular body such as a three-layered coil wound alternately at the right and left sides in the winding direction.

In accordance with an exemplary embodiment, since the first shaft 60 is flexible, the first shaft is bent along the bent shape of the second shaft 70 in a state in which the second shaft 70 is bent.

The inner diameter of the first shaft 60 can be appropriately selected, for example, the inner diameter of the first shaft 60 can be 0.4 mm to 1.9 mm and can be set to 0.7 mm as an example. The outer diameter of the first shaft 60 can be appropriately selected, for example, the outer diameter of the first shaft 60 can be 0.5 mm to 2.0 mm and can be set to 1.0 mm as an example.

A guide wire lumen into which a guide wire is insertable may be provided inside the first shaft 60. The guide wire is used to guide the rotation structure 110 when advancing the rotation structure 110 inside the blood vessel.

In accordance with an exemplary embodiment, the second shaft 70 is formed in a tubular shape. The second shaft 70 surrounds the first shaft 60 and the proximal side is connected to the second drive device 92 as illustrated in FIG. 1. In accordance with an exemplary embodiment, the second shaft 70 does not need to be essentially driven by the second drive device 92, but the second shaft 70 may be operated by a user's hand.

The second shaft 70 is bendable. Here, the bendable state means a state in which an object can be bent and a state in which an object is bent. Further, the bendable state also includes a state in which a bending structure is provided in advance and the state is maintained.

The second shaft 70 has a slit 75, which characterizes the bending shape. The bendable direction of the second shaft 70 is determined according to the shape of the pattern of the slit 75.

The outer surface of the second shaft 70 has a smooth structure, which includes a small unevenness without a cutting portion and is formed as a non-cutting portion. Accordingly, even when the outer surface of the second shaft 70 contact a normal blood vessel during the revolution of the second shaft 70, it is possible to reduce the risk of damaging the blood vessel.

The second shaft 70 has a characteristic in which a rotational force exerted at the proximal side can be transmitted to the distal side. The second shaft 70 is formed of, for example, metal such as titanium, stainless steel, and NiTi or alloy.

The inner diameter of the second shaft 70 can be appropriately selected, for example, the inner diameter of the second shaft 70 can be 1.0 mm to 2.5 mm and can be set to 1.5 mm as an example. The outer diameter of the second shaft 70 can be appropriately selected, for example, the outer diameter of the second shaft 70 can be 1.1 mm to 2.6 mm and can be set to 1.8 mm as an example.

In the example illustrated in FIG. 2, the second shaft 70 includes a step in the vicinity of the distal end of the outer sheath 80, but may not include the step. However, when the step is provided as in the embodiment and the distal end of the outer sheath 80 collides with the second shaft 70, the distal end of the outer sheath 80 can be prevented from accommodating the distal end of the second shaft 70 and exposing the distal end of the second shaft 70 from the outer sheath 80. Accordingly, a portion exposed from the outer sheath 80 in the second shaft 70 can be bent relatively easily. Further, when the second shaft 70 does not have a step and the outer sheath 80 can cover the slit 75, it is possible to prevent a decrease in suction force by blocking the slit 75 of the second shaft 70 using the outer sheath 80 from outside the second shaft 70.

The outer sheath 80 is a tubular member that covers the outside of the second shaft 70. In accordance with an exemplary embodiment, the outer sheath 80 does not move in synchronization with the rotation of the second shaft 70 and the outer sheath 80 does not rotate when the second shaft 70 rotates. In this way, since the outer sheath 80 does not rotate when the second shaft 70 is caused to revolve, it is possible to prevent a biological tissue such as a normal blood vessel from being damaged by the side surface of the outer sheath 80.

The material, which forms the outer sheath 80 is not particularly limited, for example, the outer sheath 80 material can include polyolefins such as polyethylene and polypropylene, polyamides, polyesters such as polyethylene terephthalate, fluorine polymers such as PTFE, polyetheretherketone (PEEK), polyimide, and the like can be suitably used. Further, the outer sheath 80 may be formed of a plurality of materials or a reinforcement member such as a wire may be buried in the outer sheath 80.

The inner diameter of the outer sheath 80 can be appropriately selected, for example, the inner diameter of the outer sheath 80 can be 1.2 mm to 2.9 mm and can be set to 1.9 mm as an example. The outer diameter of the outer sheath 80 can be appropriately selected, for example, the outer diameter of the outer sheath 80 can be 1.3 mm to 3.0 mm and can be set to 2.0 mm as an example.

The first drive device 91 can spin the first shaft 60 by applying a rotational force to the first shaft 60. In accordance with an exemplary embodiment, the rotation speed of the first shaft 60 can be 10,000 rpm (revolutions per minute) to 120,000 rpm. Further, the first drive device 91 can drive the first shaft 60 so that the first shaft 60 is moved in a direction parallel to the rotation axis of the first shaft 60.

In accordance with an exemplary embodiment, the second drive device 92 can cause the second shaft 70 to revolve by applying a rotational force to the second shaft 70. The rotation direction of the second shaft 70 can be selected and can be set to the same direction as the rotation direction of the first shaft 60 or the opposite direction as the rotation direction of the first shaft 60. When the rotation direction of the revolution is set to a direction opposite to the rotation direction of the spin, it is possible to reduce a movement in which the rotation structure 110 escapes from the stenotic object when the rotation structure 110 cuts the stenotic object.

In accordance with an exemplary embodiment, the second drive device 92 generally drives the rotation of the second shaft 70 so that the rotation speed of the revolution becomes slower than the rotation speed of the spin. Accordingly, it is possible to improve a cutting effect by the rotation of the rotation structure 110. In the case of the continuous revolution, the rotation speed of the second shaft 70 can be 100 rpm to 10,000 rpm, preferably 250 rpm to 8,000 rpm, and more preferably 500 rpm to 6,000 rpm. Further, since it is desirable that the rotation speed is slow when defining the directionality, the rotation speed of the second shaft 70 can be, for example, 5 rpm to 240 rpm and can be preferably 15 rpm to 120 rpm.

Further, the second drive device 92 can drive the second shaft 70 so as to move the second shaft 70 in a direction parallel to the rotation axis of the second shaft 70.

Figure 3:
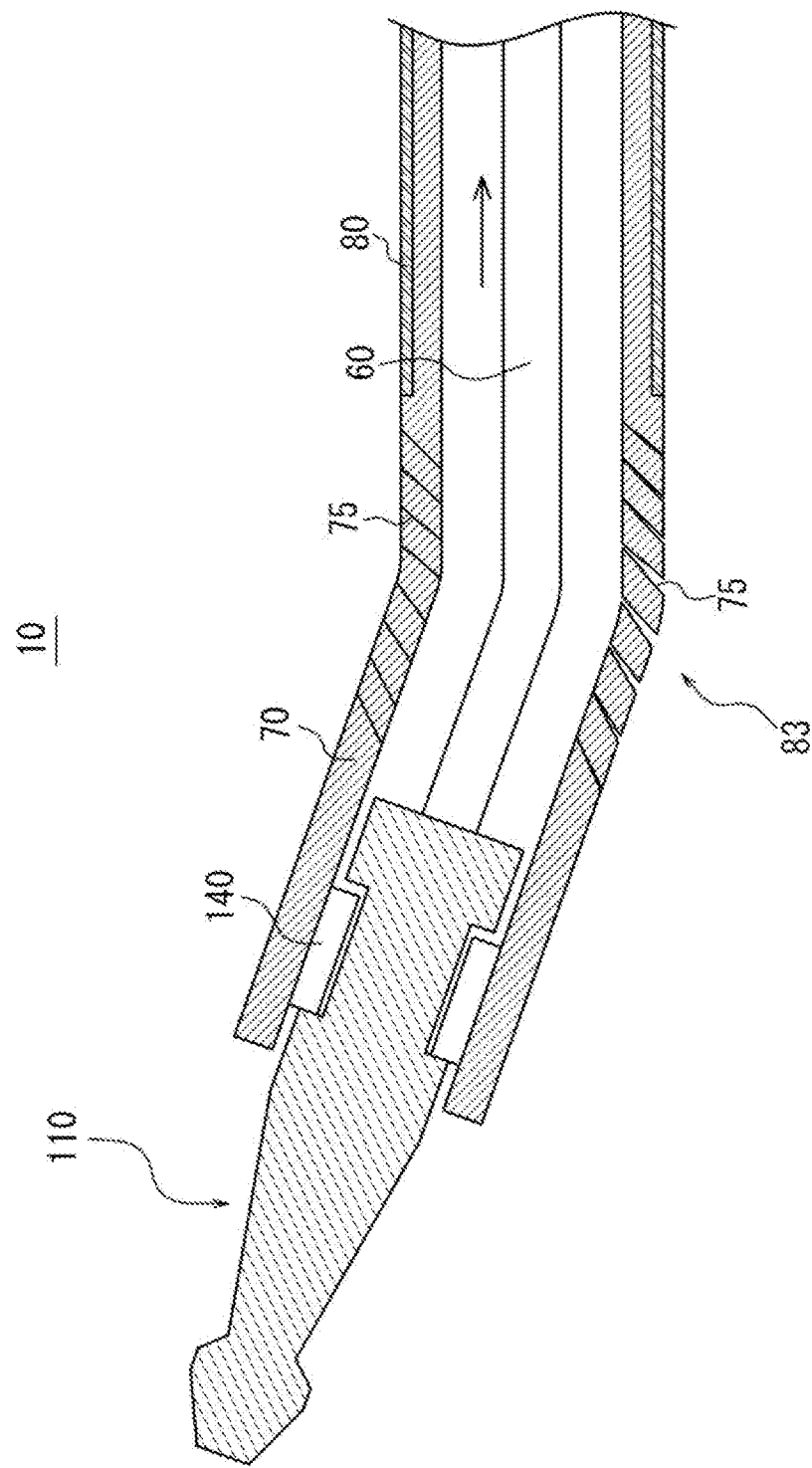
FIG. 3 is a diagram illustrating a state in which the medical device illustrated in FIG. 2 is bent.

FIG. 3 is a diagram illustrating a state in which the medical device 10 illustrated in FIG. 2 is bent. In the example illustrated in FIG. 3, the second shaft 70 has a slit 75 having a pattern, which allows the second shaft 70 to be rather easily bent toward the inner wall of the lumen. When the first shaft 60 is pulled in the proximal direction, a force exerted in the proximal direction is applied from the rotation structure 110 to the second shaft 70 through the bearing 140. Thus, the second shaft 70, which has the slit 75 having the pattern for making the second shaft 70 rather easily bendable toward the inner wall of the lumen, the second shaft 70 can be bent toward the inner wall of the lumen at the curved portion 83.

At this time, the bending degree of the second shaft 70 can be adjusted by adjusting the strength of pulling the first shaft 60. In accordance with an exemplary embodiment, the second shaft 70 is largely bent when the first shaft 60 is strongly pulled and the second shaft 70 is weakly bent when the first shaft 60 is weakly pulled (i.e., the stronger the pulling action on the first shaft 60 and the greater the bend in the second shaft 70). Further, it is possible to keep a constant bending degree of the second shaft 70 by keeping a constant force of pulling the first shaft 60. Further, it is possible to define a shape in which the second shaft 70 is bent to maximum according to the shape of the pattern of the slit 75.

Figure 4:
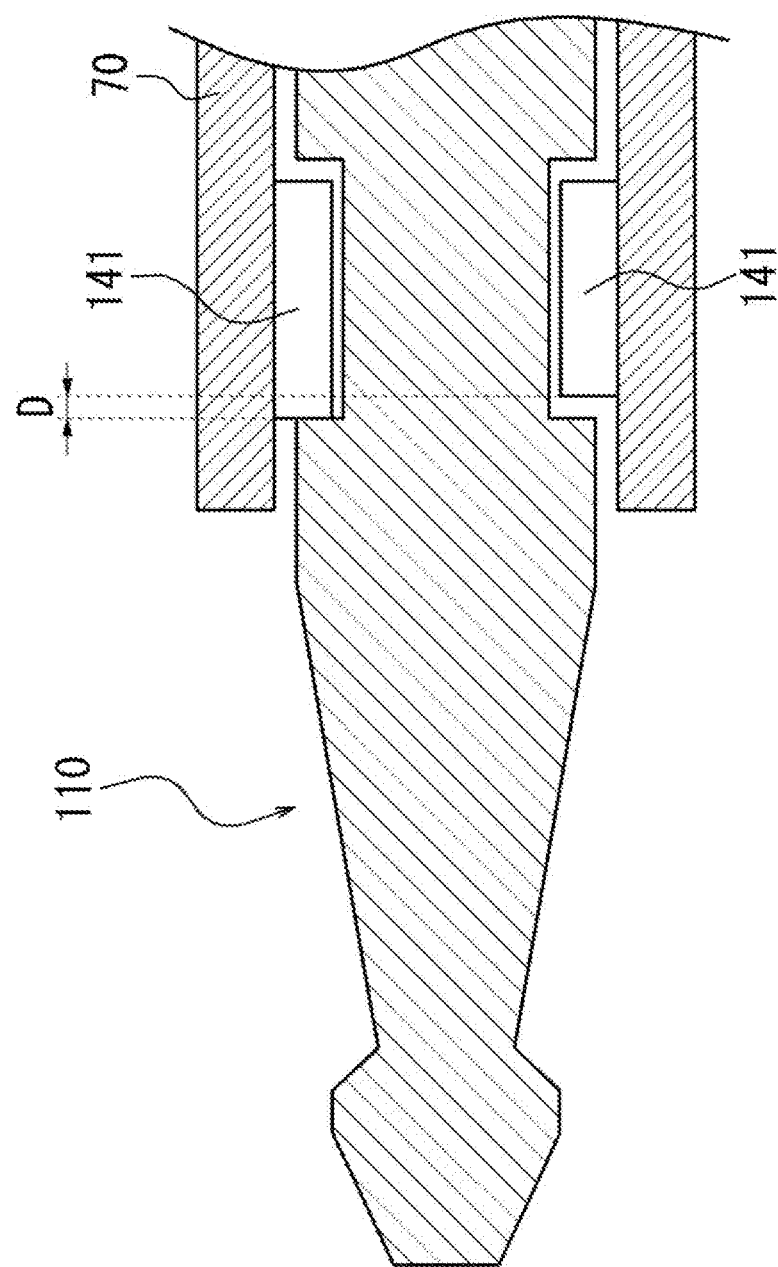
FIG. 4 is a diagram illustrating a modified example of a bearing illustrated in FIG. 2.

FIG. 4 illustrates a bearing 141, which is a modified example of the bearing 140 illustrated in FIG. 2. As illustrated in FIG. 4, the bearing 141 according to the modified example has a structure, which is not rotationally symmetric with respect to the rotation axis of the rotation structure 110. Specifically, a portion fixed to a part of the circumferential direction of the second shaft 70 extends to the distal side by a length D in the axial direction in relation to a portion fixed to another part of the circumferential direction of the second shaft 70. When the bearing 141 has such a structure, the second shaft 70 is bent in such a manner that the rotation structure 110 contacts only a circumferential direction part of the bearing 141 when the first shaft 60 is pulled. Specifically, when the first shaft 60 is pulled, only the upper side of the bearing 141 of FIG. 4 first contacts the rotation structure 110 so that a force is applied from the rotation structure 110. Accordingly, since a force exerted in the proximal direction is applied only to the upper side of the second shaft 70, which is originally rather easily bent upward through the upper side of the bearing 141, the second shaft 70 can be bent upward relatively smoothly.

FIG. 3 illustrates a state in which the second shaft 70 is bent at one curved portion 83, but the second shaft 70 may be bent at a plurality of curved portions. In this case, slits 75 are formed in a pattern to make a plurality of curved portions bendable, so that the second shaft 70 can be bent at a plurality of curved portions. Further, the second shaft 70 can be bent in various shapes according to the shape of the pattern of the slit 75. For example, the pattern of the slit 75 may be formed so that the second shaft 70 is bent relatively easily in a spiral shape. The curved portion 83 is located at the distal portion of the second shaft 70. The curved portion 83 may be located at a position within 50 mm from the proximal end of the rotation structure 110.

FIGS. 2 and 3 illustrates a case where the slit 75 defines a shape in which the second shaft 70 is relatively easily bendable, but the second shaft 70 does not have to have the slit 75. For example, in accordance with an exemplary embodiment, a shape in which the second shaft 70 is bent may be defined by the bending tendency of the second shaft 70. In a case in which the bending tendency is provided, the second shaft 70 is bent according to the bending tendency when a guiding catheter is extracted from inside or outside the second shaft 70. Further, only a state in which the bending tendency is provided in advance may be used instead of a specification capable of arbitrarily changing the bending state. The second shaft 70 can be deformed from a curved shape to a linear shape and the second shaft 70 can be deformed from the linear shape to the curved shape.

Figure 5:
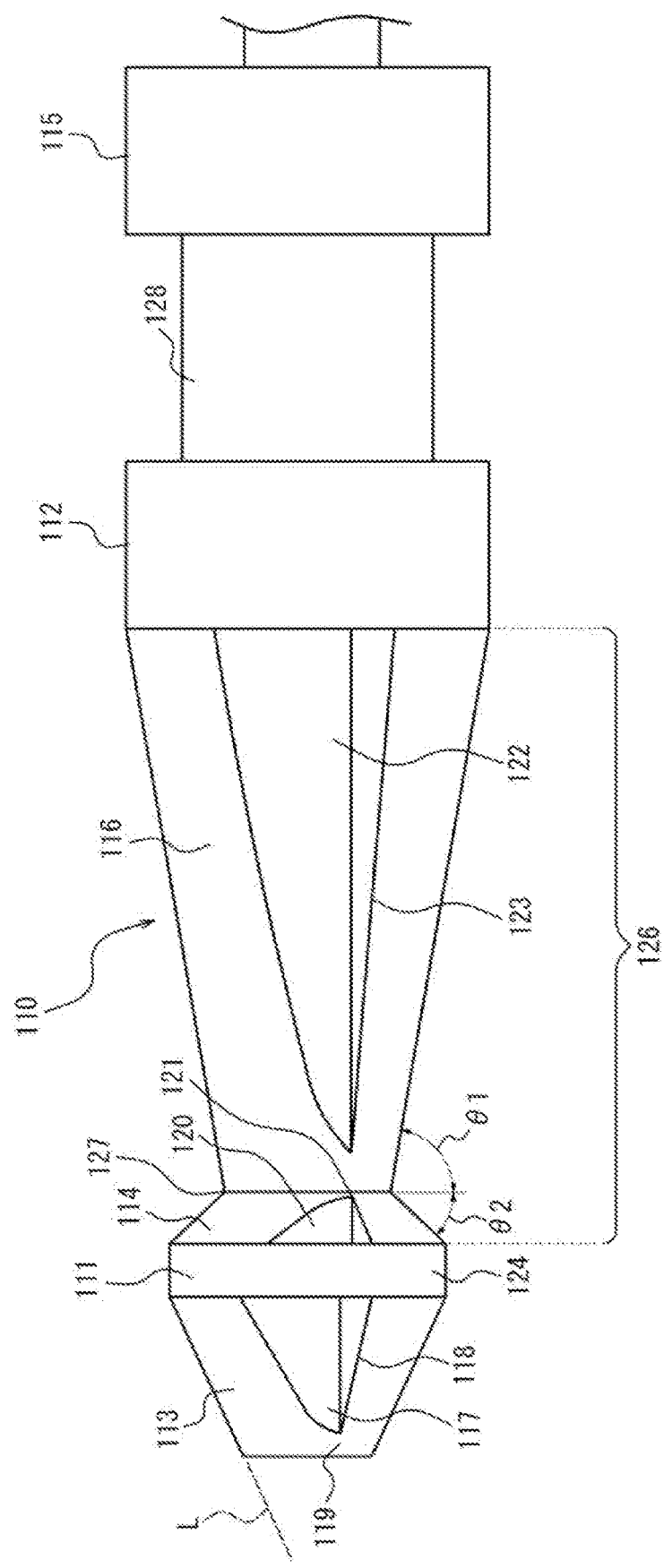
FIG. 5 is an enlarged plan view of a part including a rotation structure of FIG. 2.

Subsequently, a structure of the rotation structure 110 will be described with reference to FIG. 5. FIG. 5 is an enlarged plan view of a part including the rotation structure 110 of FIG. 2. In the description below, the "distal side" means the distal side of the rotation structure 110 and the "proximal side" means the proximal side of the rotation structure 110.

The rotation structure 110 includes the first annular portion 112 and the second annular portion 111 which is located more distal than the first annular portion 112. Further, the rotation structure 110 includes a constricted portion 126 provided between the first annular portion 112 and the second annular portion 111. The rotation structure 110 also includes a third annular portion 115 which is located at the proximal side of the first annular portion 112 and a small-diameter annular portion 128 which is located between the first annular portion 112 and the third annular portion 115 and has an outer diameter smaller than the outer diameters of the first annular portion 112 and the third annular portion 115. The bearing 140 is provided between the small-diameter annular portion 128 and the second shaft 70. The first annular portion 112 may be a proximal end of the first tapered portion 116. The second annular portion 111 may be a distal end of the second tapered portion 114.

The constricted portion 126 includes a first tapered portion 116 which is provided at the distal side of the first annular portion 112 to decrease in diameter toward the distal side and a second tapered portion 114 which is provided at the proximal side of the second annular portion 111 to decrease in diameter toward the proximal side. Further, the constricted portion 126 includes a bottom portion (i.e., lower inner edge) 127 which connects the first tapered portion 116 and the second tapered portion 114 to each other. In accordance with an exemplary embodiment, the diameter of the bottom portion 127 is smaller than the diameter of the first annular portion 112 and the diameter of the second annular portion 111. Further, the diameter of the first annular portion 112 is substantially the same as the diameter of the third annular portion 115. Furthermore, the diameter of the first annular portion 112 is larger than the diameter of the second annular portion 111. Here, the "diameter" means the diameter about the rotation axis of the rotation structure 110. The same also applies to the description below. The shape of the constricted portion 126 may be formed by the first tapered portion 116 and the second tapered portion 114 having the same maximum diameter. Further, the shape of the constricted portion 126 may be formed by the first tapered portion 116 and the second tapered portion 114 of which the maximum diameter is larger than that of the first tapered portion 116. Further, the shape of the constricted portion 126 may be formed by the first tapered portion 116 of which the maximum diameter is larger than that of the second tapered portion 114 and the second tapered portion 114. The axial length of the constricted portion 126 may be formed by the first tapered portion 116 and the second tapered portion 114 having the same axial length. The axial length of the constricted portion 126 may be formed by the first tapered portion 116 of which the axial length is longer than that of the second tapered portion 114 and the second tapered portion 114. The axial length of the constricted portion 126 may be formed by the first tapered portion 116 and the second tapered portion 114 of which the axial length is longer than that of the first tapered portion 116.

Further, the rotation structure 110 includes a third tapered portion 113 which is provided at the distal side of the second annular portion 111 to decrease in diameter toward the distal side.

In accordance with an exemplary embodiment, the first tapered portion 116 includes a first notch portion 122 which is provided in a part of the circumferential portion to be notched in a V shape in a cross-section orthogonal to the axis and a first cutting portion 123, which is a blade, is provided at the edge portion of the first notch portion 122. The first notch portion 122 may be provided only at one position or two or more positions in the circumferential portion. The first notch portion 122 may be asymmetric or symmetric. In the first notch portion 122, an angle of a surface of the first notch portion 122 opposite to the rotation direction of the rotation structure 110 is larger than that of a surface of the first notch portion 122 in the rotation direction. In accordance with an exemplary embodiment, abrasive grains, grinding stones, or the like (i.e., an abrasive material) may be electrodeposited on the first tapered portion 116. In the case where the first tapered portion 116 has, for example, abrasive grains, grinding stones or the like on the first tapered portion 116, the first tapered portion 116 becomes a fourth cutting portion. When the first tapered portion 116 includes the first cutting portion 123 of the first notch portion 122 and the fourth cutting portion having abrasive grains, grinding stones, or the like electrodeposited on the first cutting portion (the fourth cutting portion), it is possible to efficiently cut a stenotic object by the first cutting portion 123 of the first notch portion 122 and the fourth cutting portion having abrasive grains, grinding stones, or the like. Further, the first tapered portion 116 may not include the first notch portion 122, but may include only the fourth cutting portion. In accordance with an exemplary embodiment, abrasive grains can be, for example, diamond abrasive grains or the like.

In accordance with an exemplary embodiment, the second tapered portion 114 includes a second notch portion 120 which is provided in a part of the circumferential portion to be notched in a V shape in a cross-section orthogonal to the axis and a second cutting portion 121, which is a blade, is provided at the edge portion of the second notch portion 120. The second notch portion 120 may be provided only at one position or two or more positions in the circumferential portion. The second notch portion 120 may be asymmetric or symmetric. In the second notch portion 120, an angle of a surface of the second notch portion 120 opposite to the rotation direction of the rotation structure 110 is larger than an angle of a surface of the second notch portion 120 in the rotation direction. Further, abrasive grains, grinding stones, or the like may be electrodeposited on the second tapered portion 114. In that case, the second tapered portion 114 with the abrasive grains, grinding stones, or the like becomes a fifth cutting portion. When the second tapered portion 114 includes the second cutting portion 121 of the second notch portion 120 and the fifth cutting portion having abrasive grains, grinding stones, or the like electrodeposited on the second cutting portion (the fifth cutting portion), it is possible to efficiently cut a stenotic object by the second cutting portion 121 of the second notch portion 120 and the second cutting portion (the fifth cutting portion) having abrasive grains, grinding stones, or the like. Further, the second tapered portion 114 may not include the second notch portion 120, but may include only the fifth cutting portion. In accordance with an exemplary embodiment, abrasive grains can be, for example, diamond abrasive grains or the like.

In accordance with an exemplary embodiment, the third tapered portion 113 includes a third notch portion 117 which is provided in a part of the circumferential portion to be notched in a V shape in a cross-section orthogonal to the axis and a third cutting portion 118, which is a blade, is provided at the edge portion of the third notch portion 117. The third notch portion 117 may be provided only at one position or two or more positions in the circumferential portion. The third notch portion 117 may be asymmetric or symmetric. In the third notch portion 117, an angle of a surface of the third notch portion 117 opposite to the rotation direction of the rotation structure 110 is larger than that of the third notch portion 117 in the rotation direction. Further, abrasive grains, grinding stones, or the like may be electrodeposited on the third tapered portion 113. In that case, the third tapered portion 113 with the abrasive grains, grinding stones, or the like becomes a sixth cutting portion. When the third tapered portion 113 includes the third cutting portion 118 of the third notch portion 117 and the sixth cutting portion having abrasive grains, grinding stones, or the like electrodeposited on the third cutting portion (the sixth cutting portion), it is possible to efficiently cut a stenotic object by the third cutting portion 118 of the third notch portion 117 and the third cutting portion (the sixth cutting portion) having abrasive grains, grinding stones, or the like. Further, the third tapered portion 113 may not include the third notch portion 117, but may include only the sixth cutting portion. In accordance with an exemplary embodiment, abrasive grains can be, for example, diamond abrasive grains or the like.

Since the first cutting portion 123 and the third cutting portion 118 are formed in a tapered part, which decreases in diameter toward the distal side, it is possible to effectively cut the stenotic object when pressing the rotation structure 110 toward the distal side. Further, since the second cutting portion 121 is formed in a tapered part, which decreases in diameter toward the proximal side, it is possible to effectively cut the stenotic object when pulling the rotation structure 110 toward the proximal side. The axial lengths of the first notch portion 122, the second notch portion 120, and the third notch portion 117 are respectively proportional to the axial lengths of the first tapered portion 116, the second tapered portion 114, and the third tapered portion 113.

The first tapered portion 116 and the second tapered portion 114 are connected to each other by the bottom portion 127 so that an outer peripheral surface has a V shape in a longitudinal section passing through the center axis. When an angle $\theta 1$ of the first tapered portion 116 with respect to a cross-section orthogonal to the axis is compared with an angle $\theta 2$ of the second tapered portion 114 with respect to a cross-section orthogonal to the axis, the angle $\theta 2$ is equal to or smaller than the angle $\theta 1$. For this reason, it is relatively easy to hook the second cutting portion 121 to the stenotic object when pulling and cutting the stenotic object.

The second annular portion 111 may be constructed of such a shape and material such that an outer peripheral surface of the second annular portion 111 can relatively smoothly come into contact with biological tissues. For example, when the outer peripheral surface of the second annular portion 111 is constructed of the shape and material that the second annular portion 111 can relatively smoothly come into contact with the biological tissues (i.e., non-cutting purpose), the second annular portion 111 can include a first non-cutting portion 124. Accordingly, it is possible to reduce the risk of damaging the biological tissue when cutting the stenotic object. Further, the third tapered portion 113 may be provided with a second non-cutting portion 119 in which the third notch portion 117 is not formed on the outer peripheral surface of the distal side end portion throughout the entire area in the circumferential portion. In this way, since the third cutting portion 118 does not protrude outward in relation to the tangent line L between the first non-cutting portion 124 and the second non-cutting portion 119, it is possible to prevent the third cutting portion 118 from coming into contact with biological tissues and to secure high safety.

The material, which forms the rotation structure 110 is not particularly limited, for example, the rotation structure material 1110 can be stainless steel, Ta, Ti, Pt, Au, W, Ni, NiTi alloy, super steel (WC), high speed (HSS), polyolefins such as polyethylene and polypropylene, polyamides, polyesters such as polyethylene terephthalate, fluorine polymers such as PTFE, polyetheretherketone (PEEK), polyimide, and the like can be appropriately used.

In accordance with an exemplary embodiment, the rotation structure 110 includes the constricted portion 126, and the constricted portion 126 includes the second tapered portion 114 which decreases in diameter toward the proximal side, and the second tapered portion 114 includes the second cutting portion 121. In accordance with an exemplary embodiment, the second cutting portion 121 is provided in the second tapered portion 114 which decreases in diameter toward the proximal side, so that a stenotic object in a body lumen can be cut even when the rotation structure 110 is pulled (i.e., moved in a proximal direction). At this time, since a relatively strong force can be applied to the stenotic object by pulling the rotation structure 110, the medical device 10 according to the embodiment can cut the rigid stenotic object inside the body lumen. Further, at this time, since the diameter of the bottom portion 127 of the constricted portion 126 is smaller than the diameter of the first annular portion 112 and the diameter of the second annular portion 111, the risk of damaging a biological tissue such as a normal blood vessel can be reduced.

Figure 6A:
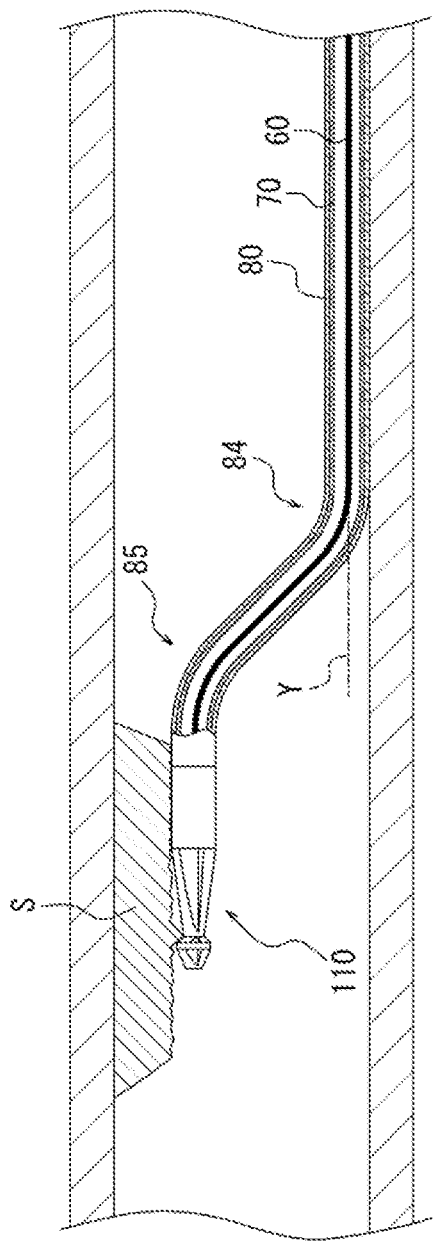
FIGS. 6A and 6B are diagrams illustrating a state in which the medical device is revolved to define a directionality and a stenotic object is cut, respectively.
Figure 6B:
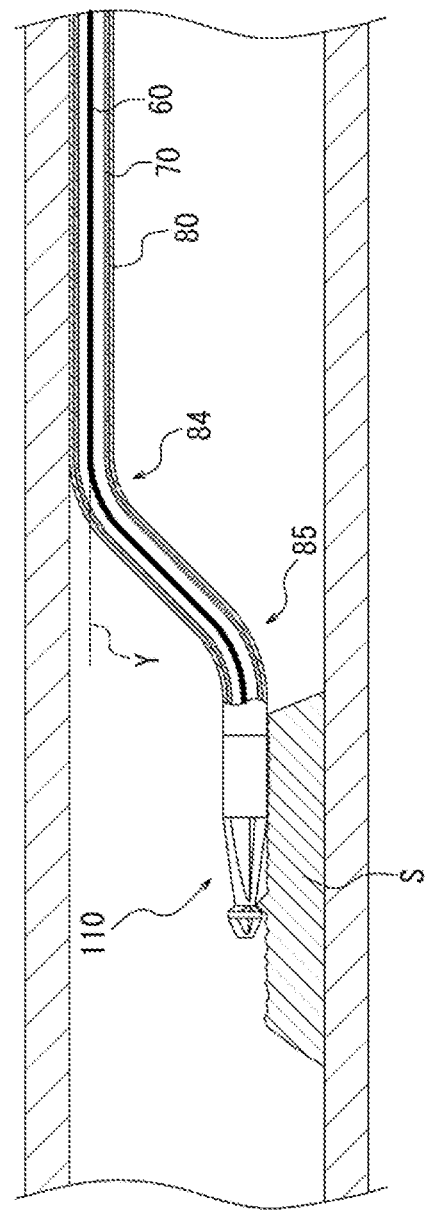

FIGS. 6A and 6B illustrate a state in which a stenotic object S inside a blood vessel is cut by the medical device 10 according to the embodiment. FIG. 6A illustrates a state in which the directionality of a part of the circumferential direction of the blood vessel (the upper side of FIG. 6A) is defined and the stenotic object S is cut and FIG. 6B illustrates a state in which the directionality of another part of the circumferential direction of the blood vessel (the lower side of FIG. 6B) is defined and the stenotic object S is cut.

In the example illustrated in FIGS. 6A and 6B, the second shaft 70 is bent at two positions of a first curved portion 84 and a second curved portion 85. As illustrated in FIGS. 6A and 6B, when the second shaft 70 is bent and the second shaft 70 is caused to revolve along the rotation axis Y, a portion located more distal than the first curved portion 84 of the second shaft 70 can be defined in a desired direction. Accordingly, the directionality can be defined so that the distal side of the medical device 10 faces the stenotic object S. Further, at this time, when the second shaft 70 is driven to revolve by the second drive device 92, the stenotic object S can be cut while ensuring a torque effect such that the rotation structure 110 is pressed against the stenotic object S. At this time, when the side of the second shaft 70, which is more proximal than the first curved portion 84 is pressed against the intravascular wall, the stenotic object S can be cut relatively easily by the rotation structure 110 by pressing the rotation structure 110 against the stenotic object S. At this time, as illustrated in FIGS. 6A and 6B, the rotation axis of the second shaft 70 is different from the rotation axis of the first shaft 60.

Figure 7:
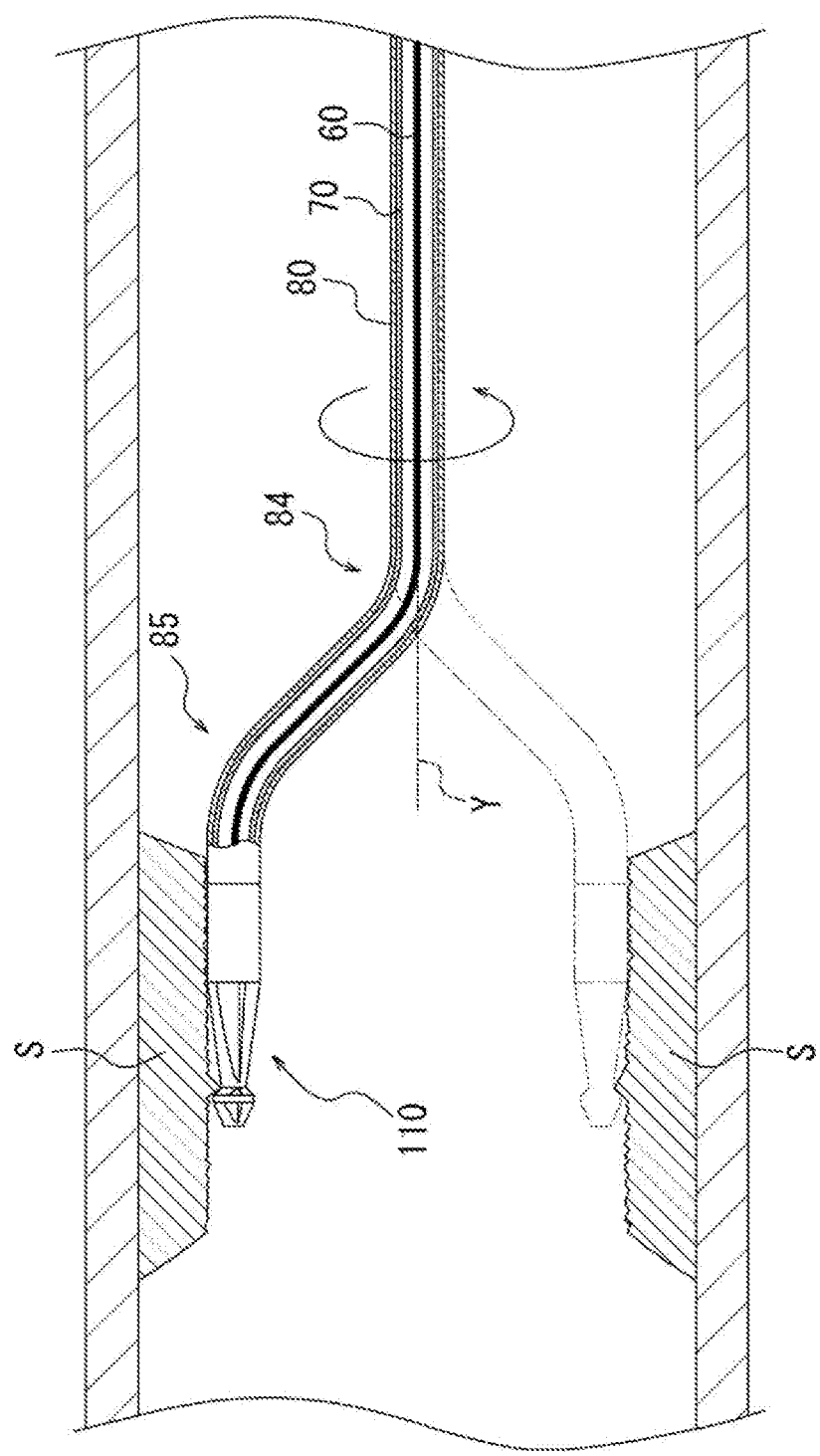
FIG. 7 is a diagram illustrating a state in which the medical device is revolved and the stenotic object is cut in a wide range.

Subsequently, FIG. 7 illustrates a state in which the stenotic object S is cut in a wide range by causing the bent second shaft 70 to revolve.

Also in the example illustrated in FIG. 7, the second shaft 70 is bent at two positions of the first curved portion 84 and the second curved portion 85 similarly to FIGS. 6A and 6B. In this state, when the second shaft 70 is caused to revolve along the rotation axis Y, the side of the second shaft 70, which is more distal than the first curved portion 84 of the second shaft 70 has relatively larger circular movement or rotation compared to the side of the second shaft 70 on the proximal side of the first curved portion 84. Accordingly, the rotation structure 110 can cut the stenotic object S in a wide range. At this time, the rotation locus (trace) of the second shaft 70 is larger than the rotation locus (trace) of the first shaft 60.

In accordance with an exemplary embodiment, the medical device 10 according to the embodiment includes the second shaft 70 which has a tubular shape surrounding the first shaft 60 and the second shaft 70 is bendable and rotatable. Accordingly, since the second shaft 70 is configured to revolve (i.e., rotate) while the medical device 10 is bent, the directionality (i.e., angle in reference to the rotation axis Y) of the medical device 10 can be defined. Further, the stenotic object can be cut by pressing the rotation structure 110 against the stenotic object while relatively ensuring a torque effect by causing the second shaft 70 to revolve.

Hereinafter, two examples (Procedures 1 and 2) will be described as an example of a procedure using the medical device 10.

Procedure 1

First, a guide wire is inserted into a blood vessel and is disposed in a lesion area. Next, the medical device 10 is disposed in the lesion area along the guide wire. The second shaft 70 is bent so that the stenotic object is pressed against the third tapered portion 113 of the medical device 10. Then, the first shaft 60 and the second shaft 70 of the medical device 10 are moved in the distal direction while being rotated about the respective axes and the stenotic object is cut by at least one of the third tapered portion 113, the third notch portion 117, and the third cutting portion 118 of the medical device 10. After the stenotic part is cut, the medical device 10 and the guide wire are extracted from the blood vessel. At this time, the second shaft 70 may be bent by pressing the proximal side of the curved portion of the second shaft 70 against the intravascular wall. Further, the rotation locus of the second shaft 70 is located outside the rotation locus of the first shaft 60.

Procedure 2

First, a guide wire is inserted into a blood vessel and is disposed in a lesion area. Next, the medical device 10 is disposed in the lesion area along the guide wire. The second shaft 70 is bent so that the stenotic object is pressed against the third tapered portion 113 of the medical device 10. Then, the first shaft 60 and the second shaft 70 of the medical device 10 are moved in the distal direction while being rotated about the respective axes and the stenotic object is cut by at least one of the third tapered portion 113, the third notch portion 117, and the third cutting portion 118 of the medical device 10. Further, the first shaft 60 and the second shaft 70 of the medical device 10 are rotated in the opposite directions to cut the lesion area which is cut by a sequential rotation according to any one of the sequence from the first to third tapered portions, the sequence from the first to third notch portions, and the sequence from the first to third cutting portions. After the stenotic part is cut, the medical device 10 and the guide wire are extracted from the blood vessel. At this time, it is possible to cut the stenotic object S without biased or uneven debulking by rotating the first shaft 60 and the second shaft 70 in the opposite directions. Further, at this time, the second shaft 70 may be bent by pressing the proximal side of the curved portion of the second shaft against the intravascular wall. Further, the rotation locus of the second shaft 70 is located outside the rotation locus of the first shaft 60.

The disclosure is not limited to the above-described embodiment and can be modified into various forms by the person skilled in the art within the technical spirit of the disclosure. For example, the body lumen into which the medical device is inserted is not limited to the blood vessel, for example, the body lumen can be a vascular tube, a ureter, a bile duct, a fallopian tube, or a hepatic duct.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object in a body lumen, the medical device comprising:
   a rotation structure having a cutting portion and a first non-cutting portion, the cutting portion including a notch having a pair of angled surfaces, and the first non-cutting portion is an annular shape that is distal to the notch;
   a first shaft configured to be connected to a center shaft of the rotation structure and configured to drive a rotation of the rotation structure;
   a second shaft having a tubular shape, the second shaft configured to surround the first shaft, the second shaft configured to be bendable at two positions including a first curved portion and a second curved portion, the second curved portion being located distally of the first curved portion;
   the second shaft being configured to be rotatable in a state in which a proximal side of the first curved portion and a distal side of the second curved portion of the second shaft are kept substantially parallel to each other; and
   wherein the rotation structure is on a distal end of the medical device and the rotation structure is configured to be kept substantially parallel to the proximal side of the first curved portion and to the distal side of the second curved portion of the second shaft when cutting the object.

2. The medical device according to claim 1, wherein a rotation locus of the second shaft is located outside a rotation locus of the first shaft.

3. The medical device according to claim 1, wherein in a state in which the second shaft is bent, a side of the second shaft more proximal than the first curved portion is pressed against an inner wall of a body lumen and the rotation structure is located opposite to the first curved portion in the body lumen.

4. The medical device according to claim 1, wherein a rotation speed of the first shaft is 10,000 rpm (revolutions per minute) to 120,000 rpm and a rotation speed of the second shaft is 5 rpm to 10,000 rpm.

5. The medical device according to claim 1, further comprising:
   a bearing which is disposed between the rotation structure and the second shaft; and
   wherein the second shaft is bent by a force transmitted from the rotation structure through the bearing when the first shaft is pulled.

6. The medical device according to claim 5, wherein the bearing is not rotationally symmetric with respect to a rotation axis of the rotation structure; and
   the second shaft is configured to be bent when the rotation structure comes into contact with only a circumferential direction part of the bearing.

7. The medical device according to claim 1, wherein a rotation axis of the second shaft is different from a rotation axis of the first shaft.

8. The medical device according to claim 2, wherein the rotation locus of the second shaft is larger than the rotation locus of the first shaft.

9. The medical device according to claim 1, wherein the second shaft has a slit, which makes the second shaft bendable.

10. The medical device according to claim 1, wherein the second shaft has a bending tendency configured to make the second shaft bendable.

11. The medical device according to claim 1, wherein the rotation structure comprises:
    an annular proximal portion;
    an annular distal portion; and
    a constricted portion provided between the annular proximal portion and the annular distal portion, the constricted portion including:
       a first tapered portion having a first cutting portion, the first tapered portion decreasing in outer diameter toward the distal side;
       a second tapered portion having a second cutting portion, the second portion decreasing in outer diameter toward the proximal side; and
       a bottom portion provided between the first tapered portion and the second tapered portion.

12. A medical device for cutting an object in a body lumen, the medical device comprising:
    a rotation structure having a cutting portion;
    a first shaft configured to be connected to a center shaft of the rotation structure and configured to drive a rotation of the rotation structure;
    a second shaft having a tubular shape, the second shaft configured to surround the first shaft and configured to be bendable at two positions including a first curved portion and a second curved portion, the second curved portion being located distally of the first curved portion; and
    a bearing which is disposed between the rotation structure and the second shaft, and wherein the second shaft is bent by a force transmitted from the rotation structure through the bearing when the first shaft is pulled.

13. The medical device according to claim 12, wherein the bearing is not rotationally symmetric with respect to a rotation axis of the rotation structure; and
    the second shaft is configured to be bent when the rotation structure comes into contact with only a circumferential direction part of the bearing.

14. A method for cutting substances inside a body lumen using a medical device including a rotation structure having a cutting portion, a first shaft configured to be connected to a center shaft of the rotation structure and configured to drive a rotation of the rotation structure, and a second shaft having a tubular shape, the second shaft configured to surround the first shaft, the second shaft configured to be bendable at two positions including a first curved portion and a second curved portion, the second curved portion being located distally of the first curved portion, the method comprising:
    inserting the medical device into the body lumen;
    rotating the second shaft in a state in which a proximal side of the first curved portion and a distal side of the second curved portion of the second shaft are kept substantially parallel to each other; and
    cutting the substances inside the body lumen with the rotation structure that is on a distal end of the medical device while rotating the second shaft and keeping the rotation structure substantially parallel to the proximal side of the first curved portion and to the distal side of the second curved portion of the second shaft.

15. The method according to claim 14, comprising:
    locating a rotation locus of the second shaft outside a rotation locus of the first shaft.

16. The method according to claim 14, wherein in a state in which the second shaft is bent, the method comprising:

pressing a side of the second shaft more proximal than the first curved portion against an inner wall of a body lumen; and locating the rotation structure opposite to the first curved portion in the body lumen.

17. The method according to claim 14, comprising:

driving the rotation of the first shaft and the second shaft by a drive device; and rotating the second shaft at a speed lower than that of the first shaft.

18. The method according to claim 14, wherein the medical device including a bearing disposed between the rotation structure and the second shaft, the method comprising:

transmitting a force from the rotation structure through the bearing when the first shaft is pulled and causing the second shaft to bend, and wherein the bearing is not rotationally symmetric with respect to a rotation axis of the rotation structure; and causing the second shaft to be bent when the rotation structure comes into contact with only a circumferential direction part of the bearing.

19. The medical device according to claim 1, wherein the notch in the cutting portion of the rotation structure is configured to be kept substantially parallel to the proximal side of the first curved portion, the distal side of the second curved portion of the second shaft, and the rotation structure.

20. The medical device according to claim 19, wherein a proximal circumferential portion of the notch is greater than a distal circumferential portion of the notch.

21. The medical device according to claim 1, wherein the rotation structure has a second non-cutting portion, the second non-cutting portion being located on a proximal end portion of the notch in the cutting portion of the rotation structure.

* * * * *